(12) United States Patent
Cecil

(10) Patent No.: US 11,446,099 B2
(45) Date of Patent: Sep. 20, 2022

(54) CONTROL ARM FOR ROBOTIC SURGICAL SYSTEMS

(71) Applicant: Covidien LP, Mansfield, MA (US)

(72) Inventor: Cameron Cecil, Boston, MA (US)

(73) Assignee: COVIDIEN LP, Mansfield, MA (US)

( * ) Notice: Subject to any disclaimer, the term of this patent is extended or adjusted under 35 U.S.C. 154(b) by 961 days.

(21) Appl. No.: 16/306,827

(22) PCT Filed: Jun. 2, 2017

(86) PCT No.: PCT/US2017/035580
§ 371 (c)(1),
(2) Date: Dec. 3, 2018

(87) PCT Pub. No.: WO2017/210499
PCT Pub. Date: Dec. 7, 2017

(65) Prior Publication Data
US 2019/0321112 A1 Oct. 24, 2019

Related U.S. Application Data

(60) Provisional application No. 62/345,537, filed on Jun. 3, 2016.

(51) Int. Cl.
*A61B 34/30* (2016.01)
*A61B 34/00* (2016.01)
(Continued)

(52) U.S. Cl.
CPC ............ *A61B 34/30* (2016.02); *A61B 34/71* (2016.02); *A61B 34/74* (2016.02); *A61B 34/76* (2016.02);
(Continued)

(58) Field of Classification Search
CPC ......... A61B 34/30; A61B 34/27; A61B 34/00; A61B 34/71; A61B 34/74; A61B 34/76;
(Continued)

(56) References Cited

U.S. PATENT DOCUMENTS

| 4,259,876 A | 4/1981 | Belyanin et al. |
| 4,353,677 A | 10/1982 | Susnjara et al. |

(Continued)

FOREIGN PATENT DOCUMENTS

| CN | 104923431 A | 9/2015 |
| EP | 0118845 A1 | 9/1984 |

(Continued)

OTHER PUBLICATIONS

Chinese First Office Action dated May 25, 2020 corresponding to counterpart Patent Application CN 201780002009.8.

(Continued)

*Primary Examiner* — Brooke Nicole Labranche

(57) ABSTRACT

A control arm for a robotic surgical system includes a base, a swivel member, a vertical member, a horizontal member, and a drive mechanism. The swivel member is rotatably supported on the base about a first axis of rotation. The vertical member is pivotally supported on the swivel member about a second axis of rotation. The horizontal member is pivotally supported by the vertical member about a third axis of rotation. The drive mechanism is disposed on the base and is configured to independently rotate the swivel member about the first axis of rotation, to pivot the vertical member about the second axis of rotation, and to pivot the horizontal member about the third axis of rotation.

16 Claims, 8 Drawing Sheets

(51) Int. Cl.
*A61B 90/00* (2016.01)
*B25J 9/04* (2006.01)
*B25J 9/06* (2006.01)
*B25J 13/02* (2006.01)

(52) U.S. Cl.
CPC .............. *A61B 90/37* (2016.02); *B25J 9/046* (2013.01); *B25J 9/06* (2013.01); *B25J 13/02* (2013.01)

(58) Field of Classification Search
CPC ... A61B 90/37; B25J 9/046; B25J 9/06; B25J 13/02; F16H 7/04
See application file for complete search history.

(56) References Cited

U.S. PATENT DOCUMENTS

| | | |
|---|---|---|
| 4,507,044 A | 3/1985 | Hutchins et al. |
| 4,806,066 A | 2/1989 | Rhodes et al. |
| 5,046,375 A | 9/1991 | Salisbury, Jr. et al. |
| 6,132,368 A | 10/2000 | Cooper |
| 6,206,903 B1 | 3/2001 | Ramans |
| 6,246,200 B1 | 6/2001 | Blumenkranz et al. |
| 6,312,435 B1 | 11/2001 | Wallace et al. |
| 6,331,181 B1 | 12/2001 | Tierney et al. |
| 6,394,998 B1 | 5/2002 | Wallace et al. |
| 6,424,885 B1 | 7/2002 | Niemeyer et al. |
| 6,441,577 B2 | 8/2002 | Blumenkranz et al. |
| 6,459,926 B1 | 10/2002 | Nowlin et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,565,554 B1 | 5/2003 | Niemeyer |
| 6,645,196 B1 | 11/2003 | Nixon et al. |
| 6,659,939 B2 | 12/2003 | Moll |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,309 B2 | 1/2005 | Whitman et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,936,042 B2 | 8/2005 | Wallace et al. |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,048,745 B2 | 5/2006 | Tierney et al. |
| 7,066,926 B2 | 6/2006 | Wallace et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,239,940 B2 | 7/2007 | Wang et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,391,177 B2 | 6/2008 | Kishi et al. |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban, III et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 | 6/2010 | Prisco |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,935,130 B2 | 5/2011 | Williams |
| 7,963,913 B2 | 6/2011 | Devengenzo et al. |
| 7,983,793 B2 | 7/2011 | Toth et al. |
| 8,002,767 B2 | 8/2011 | Sanchez |
| 8,004,229 B2 | 8/2011 | Nowlin et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,256,319 B2 | 9/2012 | Cooper et al. |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,374,723 B2 | 2/2013 | Zhao et al. |
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |

(56) References Cited

U.S. PATENT DOCUMENTS

| | | |
|---|---|---|
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,828,023 B2 | 9/2014 | Neff et al. |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart |
| 8,989,903 B2 | 3/2015 | Weir et al. |
| 9,002,518 B2 | 4/2015 | Manzo |
| 9,014,856 B2 | 4/2015 | Manzo et al. |
| 9,016,540 B2 | 4/2015 | Whitman et al. |
| 9,019,345 B2 | 4/2015 | O'Grady et al. |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |

(56) References Cited

U.S. PATENT DOCUMENTS

| | | |
|---|---|---|
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 10,939,969 B2 | 3/2021 | Swarup et al. |
| 10,939,973 B2 | 3/2021 | DiMaio et al. |
| 10,952,801 B2 | 3/2021 | Miller et al. |
| 10,965,933 B2 | 3/2021 | Jarc |
| 10,966,742 B2 | 4/2021 | Rosa et al. |
| 10,973,517 B2 | 4/2021 | Wixey |
| 10,973,519 B2 | 4/2021 | Weir et al. |
| 10,984,567 B2 | 4/2021 | Itkowitz et al. |
| 10,993,773 B2 | 5/2021 | Cooper et al. |
| 10,993,775 B2 | 5/2021 | Cooper et al. |
| 11,000,331 B2 | 5/2021 | Krom et al. |
| 11,013,567 B2 | 5/2021 | Wu et al. |
| 11,020,138 B2 | 6/2021 | Ragosta |
| 11,020,191 B2 | 6/2021 | Diolaiti et al. |
| 11,020,193 B2 | 6/2021 | Wixey et al. |
| 11,026,755 B2 | 6/2021 | Weir et al. |
| 11,026,759 B2 | 6/2021 | Donlon et al. |
| 11,040,189 B2 | 6/2021 | Vaders et al. |
| 11,045,077 B2 | 6/2021 | Stern et al. |
| 11,045,274 B2 | 6/2021 | Dachs, II et al. |
| 11,058,501 B2 | 7/2021 | Tokarchuk et al. |
| 11,076,925 B2 | 8/2021 | DiMaio et al. |
| 11,090,119 B2 | 8/2021 | Burbank |
| 11,096,687 B2 | 8/2021 | Flanagan et al. |
| 11,098,803 B2 | 8/2021 | Duque et al. |
| 11,109,925 B2 | 9/2021 | Cooper et al. |
| 11,116,578 B2 | 9/2021 | Hoffman et al. |
| 11,129,683 B2 | 9/2021 | Steger et al. |
| 11,135,029 B2 | 10/2021 | Suresh et al. |
| 11,147,552 B2 | 10/2021 | Burbank et al. |
| 11,147,640 B2 | 10/2021 | Jarc et al. |
| 11,154,373 B2 | 10/2021 | Abbott et al. |
| 11,154,374 B2 | 10/2021 | Hanuschik et al. |
| 11,160,622 B2 | 11/2021 | Goldberg et al. |
| 11,160,625 B2 | 11/2021 | Wixey et al. |
| 11,161,243 B2 | 11/2021 | Rabindran et al. |
| 11,166,758 B2 | 11/2021 | Mohr et al. |
| 11,166,770 B2 | 11/2021 | DiMaio et al. |
| 11,166,773 B2 | 11/2021 | Ragosta et al. |
| 11,173,597 B2 | 11/2021 | Rabindran et al. |
| 11,185,378 B2 | 11/2021 | Weir et al. |
| 11,191,596 B2 | 12/2021 | Thompson et al. |
| 11,197,729 B2 | 12/2021 | Thompson et al. |
| 11,213,360 B2 | 1/2022 | Hourtash et al. |
| 11,221,863 B2 | 1/2022 | Azizian et al. |
| 11,234,700 B2 | 2/2022 | Ragosta et al. |
| 11,241,274 B2 | 2/2022 | Vaders et al. |
| 11,241,290 B2 | 2/2022 | Waterbury et al. |
| 11,259,870 B2 | 3/2022 | DiMaio et al. |
| 11,259,884 B2 | 3/2022 | Burbank |
| 11,272,993 B2 | 3/2022 | Gomez et al. |
| 11,272,994 B2 | 3/2022 | Saraliev et al. |
| 11,291,442 B2 | 4/2022 | Wixey et al. |
| 11,291,513 B2 | 4/2022 | Manzo et al. |
| 2015/0230869 A1 | 8/2015 | Shim et al. |

FOREIGN PATENT DOCUMENTS

| | | |
|---|---|---|
| EP | 0122942 A1 | 10/1984 |
| KR | 10-2013-0128784 A | 11/2013 |

OTHER PUBLICATIONS

International Search Report and Written Opinion corresponding to counterpart Int'l Appln. No. PCT/US17/35580 dated Sep. 13, 2017.

U.S. Appl. No. 62/345,090, filed Jun. 3, 2016, entitled "Passive Axis System for Robotic Surgical Systems".

U.S. Appl. No. 62/345,144, filed Jun. 3, 2016, entitled "Passive Axis System for Robotic Surgical Systems".

Extended European Search Report dated Jan. 7, 2020 corresponding to counterpart Patent Application EP 17807529.7.

Chinese First Office Action dated Oct. 24, 2019 corresponding to counterpart Patent Application CN 20178002009.8.

Chinese Third Office Action dated Nov. 11, 2020 corresponding to counterpart Patent Application CN 201780002009.8.

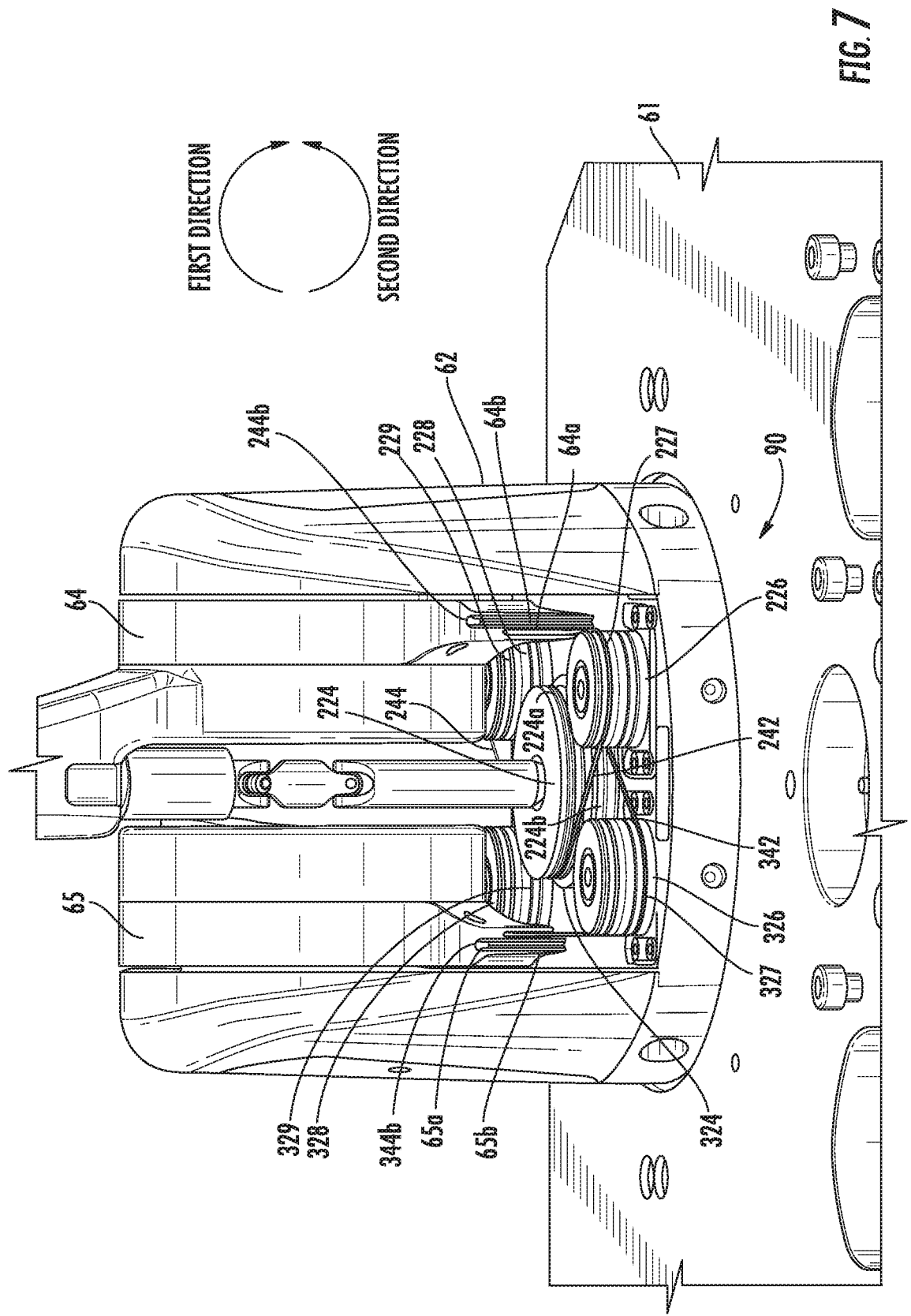

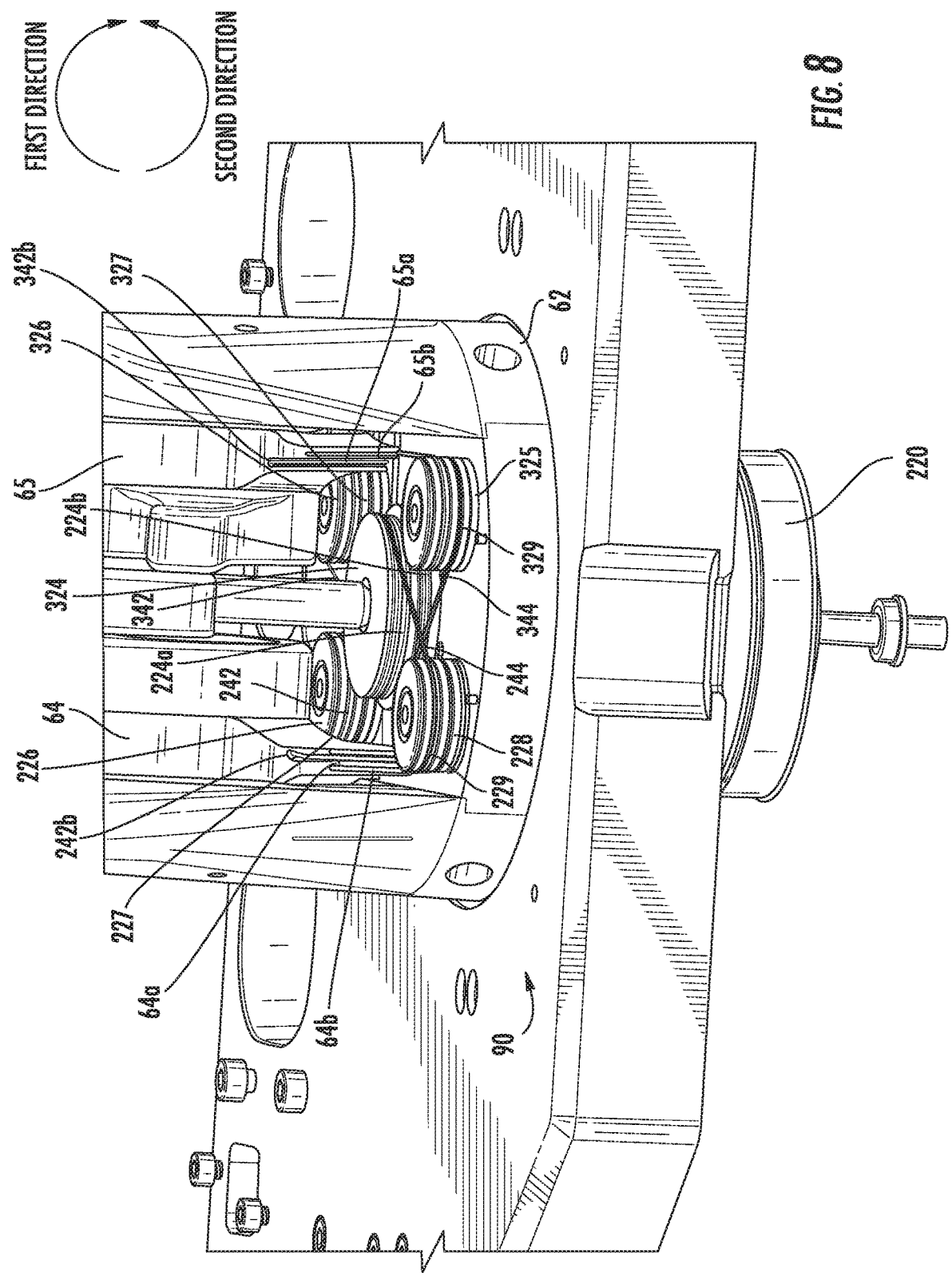

CONTROL ARM FOR ROBOTIC SURGICAL SYSTEMS

CROSS-REFERENCE TO RELATED APPLICATIONS

This application is a U.S. National Stage Application filed under 35 U.S.C. § 371(a) of International Patent Application Serial No. PCT/US2017/035580, filed Jun. 2, 2017, which claims the benefit of and priority to U.S. Provisional Patent Application Ser. No. 62/345,537, filed Jun. 3, 2016, the entire disclosure of which is incorporated by reference herein.

BACKGROUND

Robotic surgical systems have been used in minimally invasive medical procedures. During such a medical procedure, the robotic surgical system is controlled by a surgeon interfacing with a user interface. The user interface allows the surgeon to manipulate an end effector that acts on a patient. The user interface includes control arms that support a handle or gimbal that is moveable by the surgeon to control the robotic system.

SUMMARY

The present disclosure relates to drive mechanisms for manipulating a control arm of a robotic surgical system. The drive mechanism may include first, second, and third motors that are operably associated with a first, second, and third axis of rotation respectively of the control arm. The drive mechanism is configured to manipulate the control arm in response to input of a clinician with a gimbal supported by the control arm to maintain degrees of freedom (DOF) of movement of the gimbal and to prevent the control arm from interfering with other control arms of the robotic surgical system. The drive mechanism can also offset gravitation, frictional, and inertial forces of the control arm and provide haptic feedback to a clinician.

In an aspect of the present disclosure, a control arm for a robotic surgical system includes a base, a swivel member, a vertical member, a horizontal member, and a drive mechanism. The swivel member is rotatably supported on the base about a first axis of rotation. The vertical member is pivotally supported on the swivel member about a second axis of rotation. The horizontal member is pivotally supported by the vertical member about a third axis of rotation. The drive mechanism is disposed on the base to independently rotate the swivel member about the first axis of rotation, pivot the vertical member about the second axis of rotation, and pivot the horizontal member about the third axis of rotation.

In aspects, the drive mechanism includes first, second, and third drive motors. The first drive motor may affect rotation of the swivel member about the first axis of rotation, the second drive motor may affect pivoting the vertical member about the second axis of rotation, and the third drive motor may affect pivoting of the horizontal member about the third axis of rotation.

In some aspects, the drive mechanism includes the first drive motor, a rotation shaft, and a rotation flange. The rotation shaft may be disposed about the first axis of rotation and rotatably fixed to the swivel member. The rotation flange may include a cylindrical member that is disposed about the first axis of rotation and that is rotatably fixed to the rotation shaft. The cylindrical member may be operably coupled to the first drive motor to affect rotation of the swivel member about the first axis of rotation. The rotation flange may include a web that extends to an arced wall. The arced wall may form an arc about the first axis of rotation. The drive mechanism may include a first and second rotation cables that operably couple the first drive motor to the rotation flange. The first rotation cable may extend from the first drive motor in a first direction to a first end of the arced wall. The second rotation cable may extend from the first drive motor in a second direction to a second end of the arced wall.

In certain aspects, the drive mechanism includes the second drive motor, a first lower pulley, and a first upper pulley. The first lower pulley may be disposed about the first axis of rotation and be operably coupled to the second drive motor by a first pair of drive cables. The first upper pulley may be disposed about the first axis of rotation and be rotatably fixed to the first lower pulley. The first upper pulley may be operably coupled to the vertical member to pivot the vertical member about the second axis of rotation. The drive mechanism may include first and second idlers. The vertical member may define first and second vertical member grooves and include first and second pivot cables. The first pivot cable may be disposed about the first upper pulley, around the first idler, and within the first vertical member groove. The second pivot cable may be disposed about the first upper pulley, around the second idler, and within the second vertical member groove. The first and second pivot cables may operably couple the first upper pulley to the vertical member. The drive mechanism may include a first pulley shaft that rotatably fixes the first lower pulley to the first upper pulley. The drive mechanism may also include second upper and lower pulleys that are rotatably fixed to one another by a second pulley shaft that is disposed about the first pulley shaft.

In particular aspects, the control arm includes a support member and a support arm. The support arm may be pivotally supported by the swivel member about the second axis of rotation. Alternatively, the support arm may be pivotally supported by the swivel member about an axis parallel to and offset from the second axis of rotation. The support member may be pivotally coupled to the support arm and the horizontal member to pivot the horizontal member about the third axis of rotation in response to pivoting the support arm about the second axis of rotation. The drive mechanism may include a third drive motor, a second lower pulley, and a second upper pulley. The second lower pulley may be disposed about the first axis of rotation and be operably coupled to the third drive motor by a second pair of drive cables. The second pulley may be disposed about the first axis of rotation and be rotatably fixed to the second lower pulley. The second upper pulley may be operably coupled to the support arm to pivot the support arm about the second axis of rotation. The drive mechanism includes third and fourth idlers and third and fourth pivot cables. The support arm may divide first and second support grooves. The third pivot cable may be disposed about the second upper pulley, around the third idler, and within the first support groove. The fourth pivot cable may be disposed about the second upper pulley, around the fourth idler, and within the second support groove. The third and fourth pivot cables may operably couple the second upper pulley to the support arm.

In another aspect of the present disclosure, a method of manipulating a control arm including a base, a swivel member, a vertical member, and a horizontal member includes activating a first drive motor to rotate the swivel member about a first axis of rotation, activating a second drive motor to pivot the vertical member about a second axis of rotation, and activating a third drive motor to pivot the horizontal member about a third axis of rotation. The first axis of rotation may be defined between the swivel member and the base. The second axis of rotation may be defined between the vertical member and the swivel member. The third axis of rotation may be defined between the horizontal member and the vertical member.

In aspects, activating the first drive motor to rotate the swivel member about the first axis of rotation includes rotating a flange rotatably disposed on a lower side of the base member about the first axis of rotation to rotate the swivel member. Rotating the flange may include wrapping a first drive cable around a drive shaft of the first drive motor and unwrapping a second drive cable from around the drive shaft of the first drive motor. The first and second drive cables may be disposed about an arced wall of the flange.

In some aspects, activating the second drive motor to pivot the vertical member about the second axis of rotation includes rotating a first lower pulley about the first axis of rotation which affects rotation of a first upper pulley about the first axis of rotation which affects rotation of the vertical member about the second axis of rotation. Rotation of the first lower pulley about the first axis of rotation may include wrapping a first drive cable about a drive shaft of the second drive motor and unwrapping a second drive cable about the drive shaft of the second drive motor.

In certain aspects, activating the third drive motor to pivot the horizontal member about the third axis of rotation includes rotating a second lower pulley about the first axis of rotation which affects rotation of a second upper pulley about the first axis of rotation which affects rotation of the horizontal member about the third axis of rotation. Rotation of the second upper pulley about the first axis of rotation affects rotation of the support member about the second axis of rotation or an axis parallel to and offset from the second axis of rotation which affects rotation of the horizontal member about the third axis for rotation. Rotating the second lower pulley about the first axis of rotation may include wrapping a first drive cable about a drive shaft of the third drive motor and unwrapping a second drive cable about the drive shaft of the third drive motor.

Further details and aspects of exemplary embodiments of the present disclosure are described in more detail below with reference to the appended figures.

BRIEF DESCRIPTION OF THE DRAWINGS

Various aspects of the present disclosure are described hereinbelow with reference to the drawings, which are incorporated in and constitute a part of this specification, wherein:

FIG. 7 is an enlarged rear perspective view of the base of the control arm of FIG. 2; and FIG. 8 is an enlarged front perspective view of the base of the control arm of FIG. 2.

DETAILED DESCRIPTION

Figure 1:
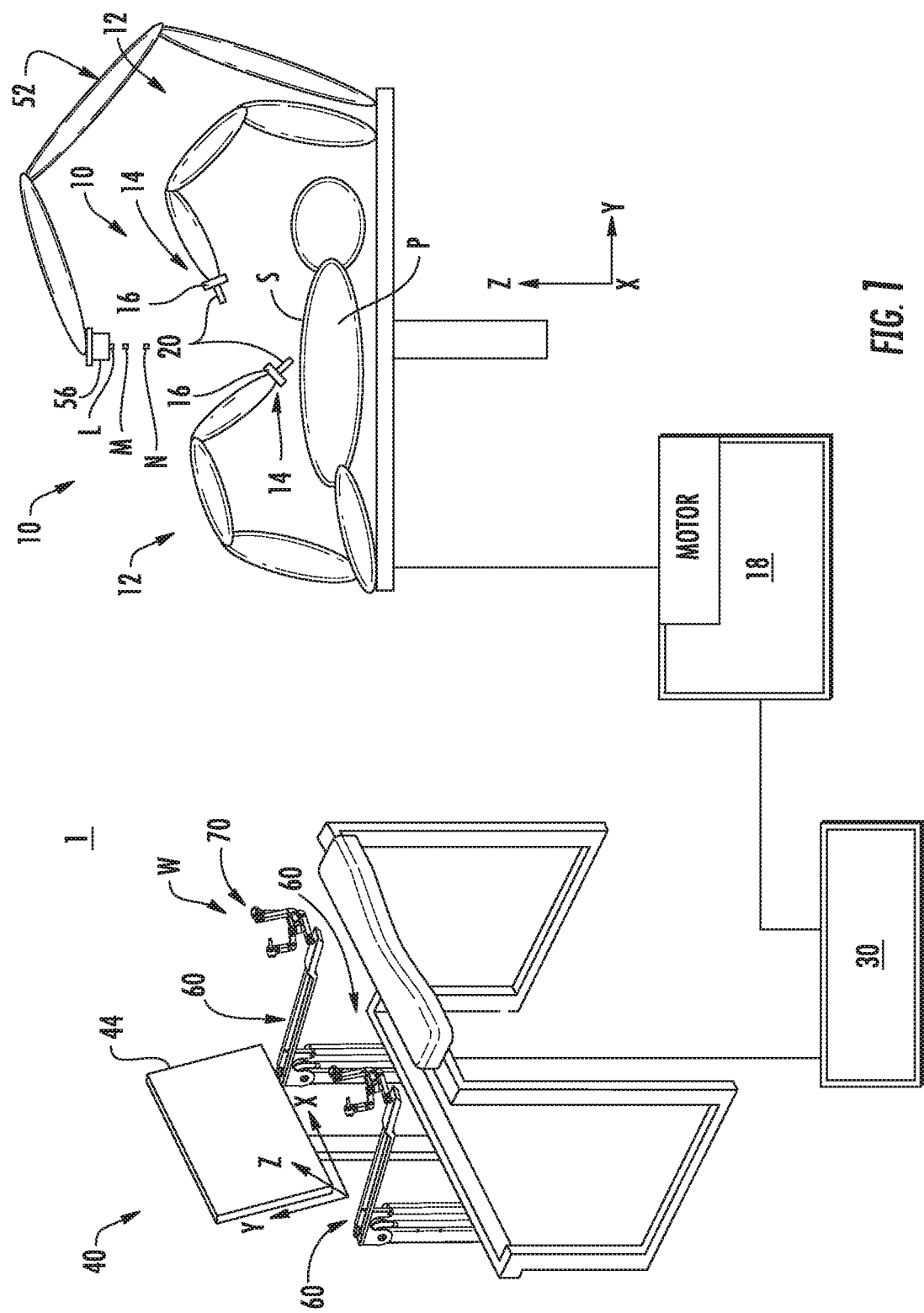
FIG. 1 is a schematic illustration of a user interface and a robotic system in accordance with the present disclosure.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel.

The present disclosure relates generally to drive mechanisms including first, second, and third motors that are operably associated with first, second, and third axes of rotation of a control arm of a robotic surgical system by a first, second, and third pair of drive cables, respectively.

Referring to FIG. 1, a robotic surgical system 1 is shown generally as a robotic system 10, a processing unit 30, and a user interface 40. The robotic system 10 generally includes linkages 12 and a robot base 18. The linkages 12 moveably support an end effector or tool 20 which is configured to act on tissue. The linkages 12 may be in the form of arms or links each having an end 14 that supports an end effector or tool 20 which is configured to act on tissue. In addition, the ends 14 of the linkages 12 may include an imaging device 16 for imaging a surgical site "S". The user interface 40 is in communication with robot base 18 through the processing unit 30.

The user interface 40 includes a display device 44 which is configured to display three-dimensional images. The display device 44 displays three-dimensional images of the surgical site "S" which may include data captured by imaging devices 16 positioned on the ends 14 of the linkages 12 and/or include data captured by imaging devices that are positioned about the surgical theater (e.g., an imaging device positioned within the surgical site "S", an imaging device positioned adjacent the patient "P", imaging device 56 positioned at a distal end of an imaging linkage 52). The imaging devices (e.g., imaging devices 16, 56) may capture visual images, infra-red images, ultrasound images, X-ray images, thermal images, and/or any other known real-time images of the surgical site "S". The imaging devices transmit captured imaging data to the processing unit 30 which creates three-dimensional images of the surgical site "S" in real-time from the imaging data and transmits the three-dimensional images to the display device 44 for display.

The user interface 40 also includes control arms 60 that each support a gimbal 70 having an input handle attached to allow a clinician to manipulate the robotic system 10 (e.g., manipulate the linkages 12, the ends 14 of the linkages 12, and/or the tools 20). Each of the gimbals 70 is in communication with the processing unit 30 to transmit control signals thereto and to receive feedback signals therefrom. Additionally or alternatively, each of the gimbals 70 may include control interfaces or input devices (not shown) which allow the surgeon to manipulate (e.g., clamp, grasp, fire, open, close, rotate, thrust, slice, etc.) and/or to move the tools 20 supported at the ends 14 of the linkages 12.

Each of the gimbals 70 is moveable to move the ends 14 of the linkages 12 within a surgical site "S". The three-dimensional images on the display device 44 are orientated such that movement of the gimbals 70 moves the ends 14 of the linkages 12 as viewed on the display device 44. It will be appreciated that the orientation of the three-dimensional images on the display device may be mirrored or rotated relative to view from above the patient "P". In addition, it will be appreciated that the size of the three-dimensional images on the display device 44 may be scaled to be larger or smaller than the actual structures of the surgical site "S" permitting the surgeon to have a better view of structures within the surgical site "S". As the gimbal 70 is moved, the tools 20 are moved within the surgical site "S". Movement of the tools 20 may also include movement of the ends 14 of the linkages 12 which support the tools 20.

For a detailed discussion of the construction and operation of a robotic surgical system 1, reference may be made to U.S. Pat. No. 8,828,023, the entire contents of which are incorporated herein by reference.

Figure 2:
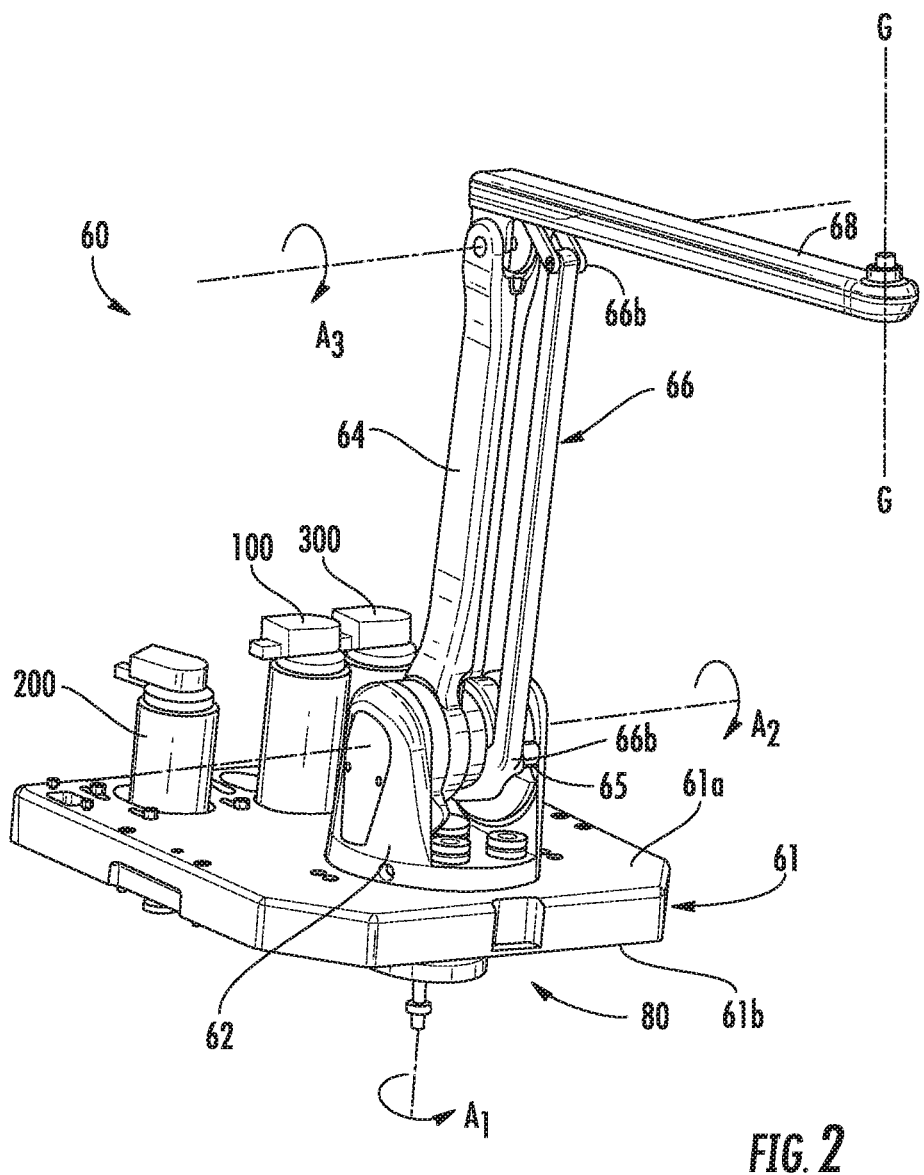
FIG. 2 is a front perspective view of a control arm of the user interface of FIG. 1 in accordance with the present disclosure.

Referring to FIG. 2, a control arm 60 of the user interface 40 (FIG. 1) is provided in accordance with the present disclosure. The control arm 60 includes a base 61, a swivel member 62, a vertical member 64, a support arm 65, a support member 66, and a horizontal member 68. The base 61 rotatably supports the swivel member 62 about a first axis of rotation $A_1$. The swivel member 62 pivotally supports the vertical member 64 and the support arm 65 about a second axis of rotation $A_2$. It is envisioned that the support arm 65 may pivot about an axis of rotation that is parallel to and offset from the second axis of rotation $A_2$. The support arm 65 supports a lower end 66a of the support member 66 which may be in substantial parallel relationship with the vertical member 64. It is contemplated that the support member 66 may be askew from the vertical member 64. The vertical member 64 and the support member 66 pivotally support the horizontal member 68 about a third axis of rotation $A_3$. The third axis of rotation $A_3$ may pass through the vertical member 64 and the horizontal member 68; alternatively, the third axis of rotation $A_3$ may be defined remote to the vertical member 64 and the horizontal member 68. The horizontal member 68 rotatably supports a gimbal 70 (FIG. 1) about a gimbal axis G-G.

The base 61 includes a drive mechanism 80 for manipulating the control arm 60 about each of the first, second, and third axes of rotation $A_1$, $A_2$, $A_3$. The drive mechanism 80 may manipulate the control arm 60 to provide force feedback to a clinician interfacing with a gimbal 70 (FIG. 1) supported by the control arm 60. The drive mechanism 80 may also manipulate the control arm 60 to reposition members of the control arm 60 during a surgical procedure. The drive mechanism 80 may include a passive axis system that passively repositions members of the control arm 60 to maintain degrees of freedom (DOF) during a surgical procedure. For a detailed description of an exemplary passive axis system references can be made to U.S. Provisional Patent Application No. 62/345,090, filed Jun. 3, 2016 and U.S. Provisional Patent Application No. 62/345,144, filed Jun. 3, 2016, both entitled "PASSIVE AXIS SYSTEM FOR ROBOTIC SURGICAL SYSTEMS," the entire contents of which are hereby incorporated by reference. In addition, the drive mechanism 80 may manipulate the control arm 60 to prevent the control arm 60 from interfering with another control arm of the user interface 40. Further, the drive mechanism 80 may manipulate the control arm 60 to offset gravitational, frictional, and inertial forces of the control arm 60. In addition, the drive mechanism may provide haptic feedback.

Figure 3:
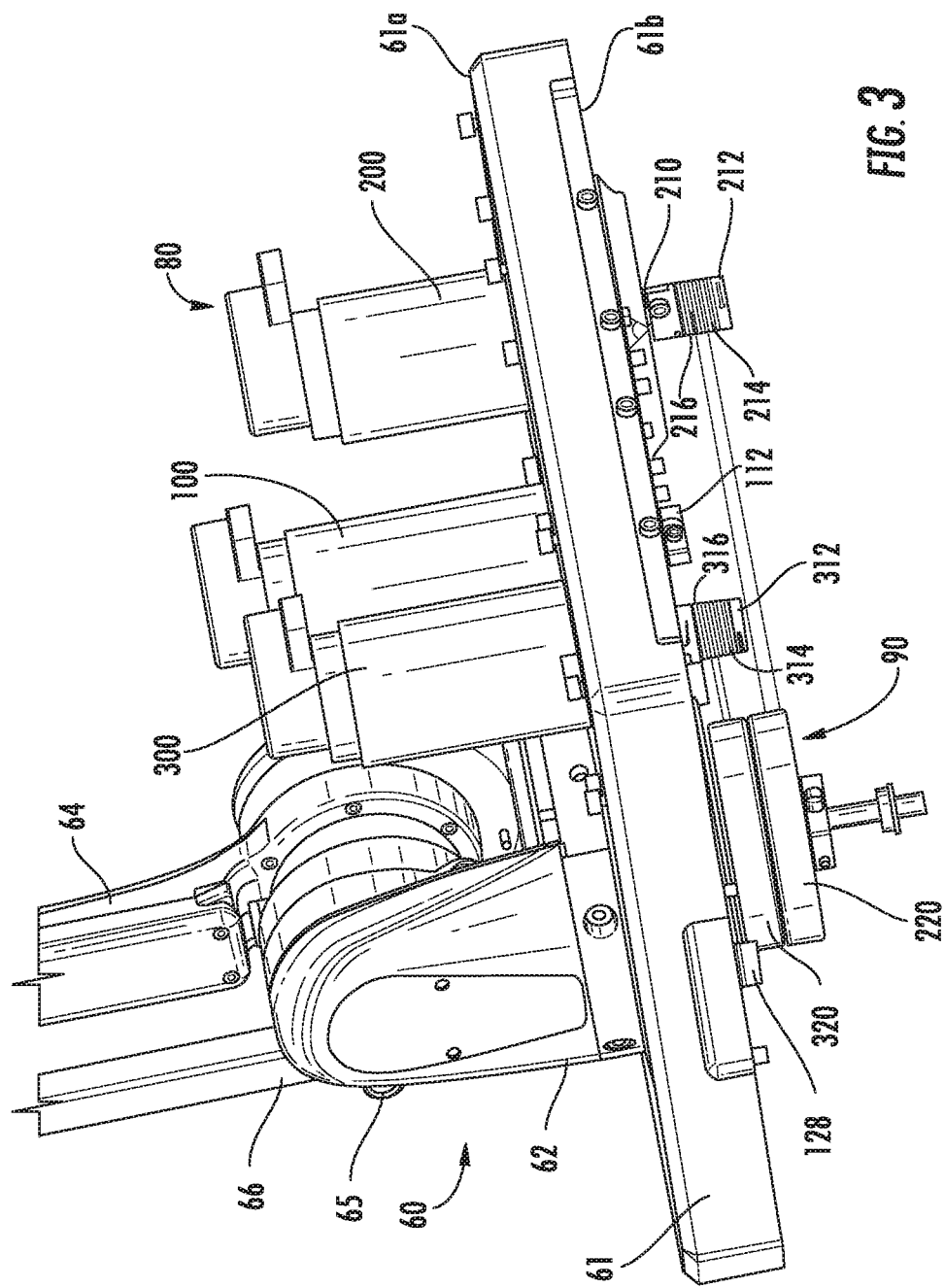
FIG. 3 is a rear perspective view of a base of the control arm of FIG. 2.
Figure 4:
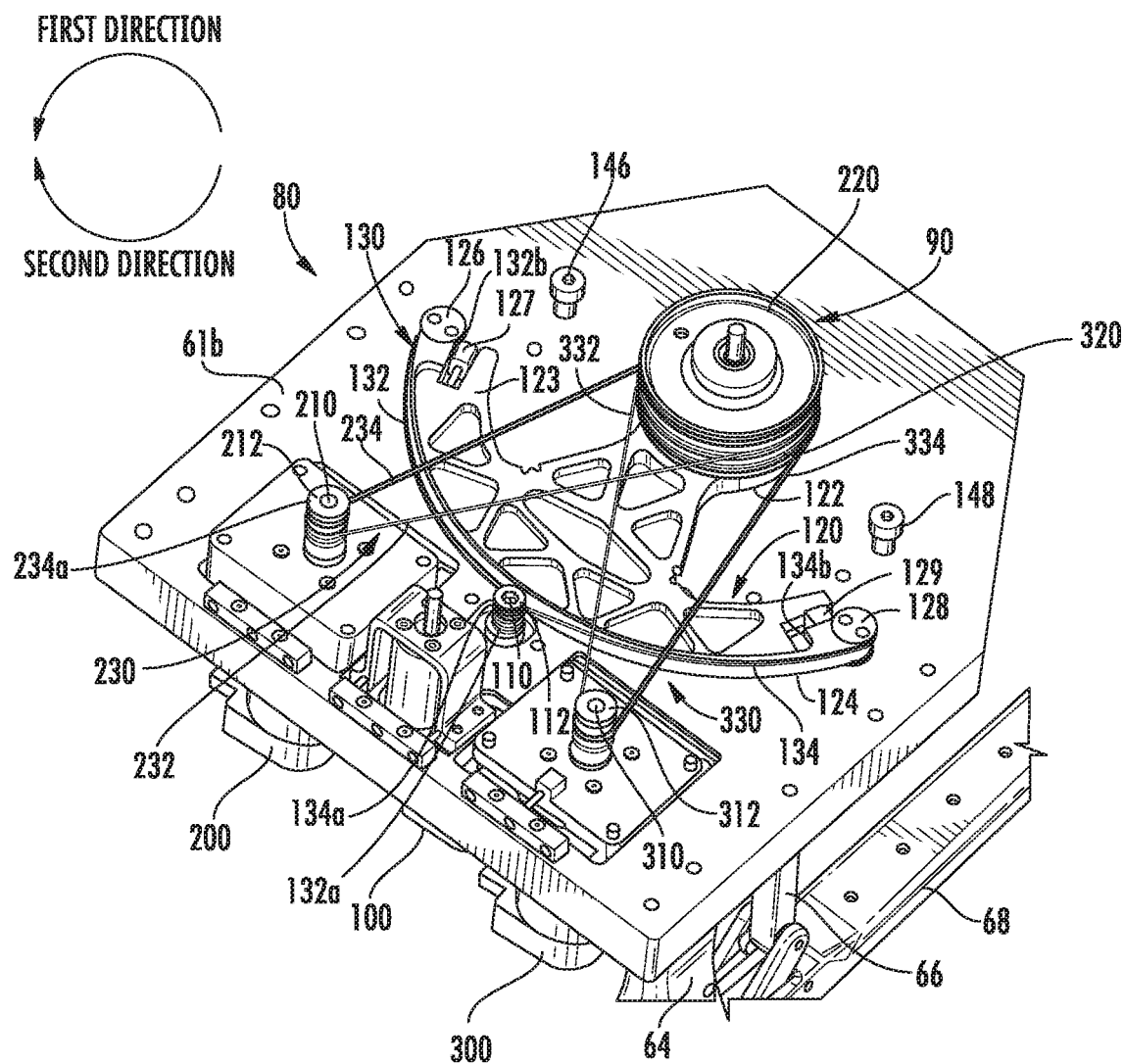
FIG. 4 is a lower perspective view of the base of the control arm of FIG. 3.
Figure 5:
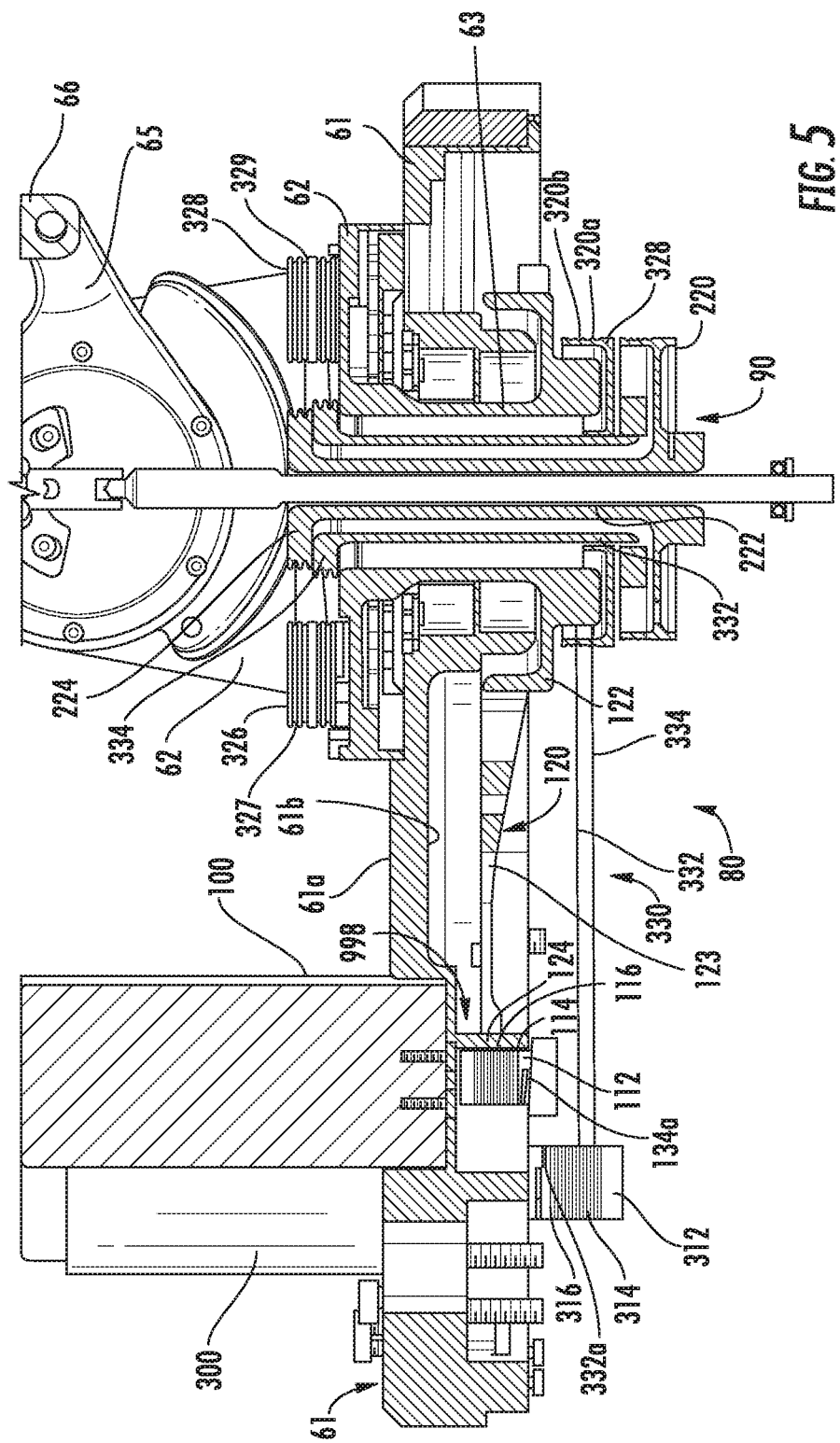
FIG. 5 is a cross-sectional view taken along section line 5-5 of FIG. 4.

With additional reference to FIGS. 3-5, the drive mechanism 80 includes a first drive motor 100, a second drive motor 200, and a third drive motor 300. The first drive motor 100 manipulates the control arm 60 about the first axis of rotation $A_1$ and includes a first drive shaft 110 that extends through the base 61 from an upper or first side 61a of the base 61 to a lower or second side 61b of the base 61. The first drive shaft 110 includes a first spindle 112 that is rotatably coupled to the first drive shaft 110. An outer surface of the first spindle 112 defines a first helical groove 114 and a second helical groove 116. As shown, the first helical groove 114 is in communication with the second helical groove 116 to form a single continuous helical groove. The swivel member 62 includes a rotation shaft 63 that is engaged by a rotation flange 120. The rotation flange 120 includes a cylindrical member 122 disposed about the rotation shaft 63 such that the rotation flange 120 rotates in concert with the swivel member 62. The rotation flange 120 and the swivel member 62 rotate about the first axis of rotation $A_1$ relative to the base 61.

The rotation flange 120 includes a web 123 that extends from the cylindrical member 122 to an arced or curved wall 124 having a first end 126 and a second end 128. Each end 126, 128 of the arced wall 124 is rounded and includes a cable catch 127, 129, respectively. It is envisioned that the curved wall 124 can form a circular wall (not shown).

The drive mechanism 80 includes a first pair of cables 130 that manipulate or rotate the rotation flange 120 about the first axis of rotation $A_1$. The first pair of cables 130 includes a first cable 132 and a second cable 134. The first cable 132 has an end 132a that is secured to the spindle 112. The first cable 132 wraps around the first spindle 112 in a first direction (i.e., counter-clockwise as shown in FIG. 3) from the end 132a. The first spindle 112 defines a first helical groove 114 that receives the first cable 132 as the first cable 132 wraps around the first spindle 112. The first cable 132 extends from the first spindle 112 about the arced wall 124 to the first end 126 of the arced wall 124 with the end 132b of the first cable 132 wrapped around the first end 126 and secured within the cable catch 127 at the first end 126.

The second cable 134 has an end 134a that is secured to the first spindle 112. The second cable 134 wraps around the first spindle 112 in a second direction (i.e., clockwise as shown in FIG. 3) opposite the first direction from the end 134a. The first spindle 112 defines a second helical groove 116 that receives the second cable 134 as the second cable 134 wraps around the first spindle 112. The second cable 134 extends from the first spindle 112 about the arced wall 124 to the second end 128 of the arced wall 124 with the end 134b of the second cable 134 wrapped around the second end 128 of the arced wall 128 and secured within the cable catch 129 at the second end 128.

To rotate the swivel member 62 relative to the base 61, the first drive motor 100 is activated to rotate the first spindle 112 in a first direction (i.e., counter-clockwise as shown in FIG. 4). As the first spindle 112 is rotated in the first direction, the end 134b of the second cable 134 is tensioned to draw the second end 128 of the arced wall 124 towards the first spindle 112 to rotate the rotation flange 120 in the second direction (i.e., clockwise as shown in FIG. 4). As the first spindle 112 is rotated in the first direction, the first cable 132 is let out from around the first spindle 112 such that the end 132b of the first cable 132 is free to move away from the spindle 112. As detailed above, the rotation flange 120 is rotatably coupled to the swivel member 62 such that as the rotation flange 120 is rotated relative to the base 61, the swivel member 62 is rotated relative to the base 61 in the same direction as the rotation flange 120 (e.g., when the rotation flange 120 is rotated clockwise as shown in FIG. 4, the swivel base 61 is rotated counter-clockwise as shown in FIG. 2).

Similarly, to rotate the swivel member 62 in the other direction relative to the base 61, the first spindle 112 is rotated in the second direction. As the first spindle 112 is rotated in the second direction, the end 132b of the first cable 132 is tensioned to draw the first end 126 of the arced wall 124 towards the first spindle 112 to rotate the rotation flange 120 in the first direction. As the first spindle 112 is rotated in the second direction, the second cable 134 is let out from around the first spindle 112 such that the end 134b of the second cable 134 is free to move away from the spindle 112. Further, it will be appreciated that by tensioning one cable (e.g., second cable 134) while letting out the other cable (e.g., first cable 132) the angular position of the rotation flange 120 relative to the base 61 can be precisely controlled.

Rotation of the rotation flange 120 may be limited by stops 146, 148 that extend from the lower surface 61b of the base 61. The stop 146 is positioned adjacent the first end 126 of the arced wall 124 and is engaged by the web 123 of the rotation flange 120 to limit rotation of the swivel member 62 in the second direction. The stop 148 is positioned adjacent the second end 128 of the arced wall 124 and is engaged by the web 123 of the rotation flange 120 to limit rotation of the swivel member 62 in the first direction.

Referring to FIGS. 2-8, the second drive motor 200 manipulates the vertical member 64 of the control arm 43 about the second axis of rotation $A_2$. The second drive motor 200 includes a second drive shaft 210 that extends through the base 61 from the upper or first side 61a to the lower or second side 61b of the base 61. The second drive shaft 210 includes a second spindle 212 that is rotatably coupled to the second drive shaft 210. The base 61 includes a pulley assembly 90 that is rotatably disposed about the first axis of rotation $A_1$. The pulley assembly 90 includes a lower inner pulley 220, an inner pulley shaft 222, an upper inner pulley 224, a first upper idler 226 and a second upper idler 228.

The drive mechanism 80 of the control arm 43 includes a pair of drive cables 230 and a pair of idler cables 240 that manipulate or pivot the vertical member 64 about the second axis of rotation $A_2$. The pair of drive cables 230 includes a first drive cable 232 that has a first end 232a secured to the second spindle 212. The first drive cable 232 wraps around the second spindle 212 in the second direction (i.e., clockwise as shown in FIG. 3) from end 232a. The second spindle 212 defines a first helical groove 214 that receives the first drive cable 232 as the first drive cable 232 wraps around the second spindle 212. The first drive cable 232 extends from the second spindle 212 to the lower inner pulley 220. The first drive cable 232 wraps around the lower inner pulley 220 in the second direction with a second end of the first drive cable 232 secured to the lower inner pulley 220. The lower inner pulley 220 defines a first recess 221a about the outer surface thereof that receives the first drive cable 232.

The pair of drive cables 230 also includes a second drive cable 234 that has a first end 234a secured to the second spindle 212. The second drive cable 234 wraps around the second spindle 212 in the first direction (i.e., counter-clockwise as shown in FIG. 3) from end 234a. The second spindle 212 defines a second helical groove 216 that receives the second drive cable 234 as the second drive cable 234 wraps around the second spindle 212. The second drive cable 234 extends from the second spindle 212 to the lower inner pulley 220. The second drive cable 234 wraps around the lower inner pulley 220 in the first direction with a second end of the second drive cable 234 secured to the lower inner pulley 220. The lower inner pulley 220 defines a second recess 221b about the outer surface that receives the second drive cable 234.

The lower inner pulley 220 is rotatably fixed to the upper inner pulley 224 by the inner pulley shaft 222. The pair of idler cables 240 includes a first idler cable 242 that has a first end 242a secured to the upper inner pulley 224. The upper inner pulley 224 defines a first recess 224a that receives the first idler cable 242 that wraps around the upper inner pulley 224 in the second direction (i.e., counter-clockwise as shown in FIG. 5). The first idler cable 242 extends from the upper inner pulley 224 to the first upper idler 226 that is rotatably supported on a post 206 of the base 61. The first upper idler 226 defines a recess 227 that receives the first idler cable 242 as the first idler cable 242 wraps around the first upper idler 226 in the second direction. The first idler cable 242 extends from the first upper idler 226 to the vertical member 64. With particular reference to FIG. 7, the vertical member 64 defines a first groove 64a that receives the first idler cable 242. A second end 242b of the first idler cable 242 is secured in the first groove 64a of the vertical member 64. The pair of idler cables 240 includes a second idler cable 244 that has a first end 244da secured to the upper inner pulley 224. The upper inner pulley 224 defines a second recess 224b that receives the second idler cable 244 that wraps around the upper inner pulley 224 in the first direction (i.e., clockwise as shown in FIG. 7). The second idler cable 244 extends from the upper inner pulley 224 to the second upper idler 228 that is rotatably supported on a post of the base 61. The second upper idler 228 defines a recess 229 that receives the second idler cable 244 as the second idler cable 244 wraps around the second upper idler 228 in the first direction. The second idler cable 244 extends from the second upper idler 228 to the vertical member 64. With particular reference to FIG. 8, the vertical member 64 defines a second groove 64b that receives the second idler cable 244. An end 244b of the second idler cable 244 is secured in the second groove 64b of the vertical member 64.

To pivot the vertical member 64 about the second axis of rotation $A_2$, the second drive motor 200 is energized to rotate the second spindle 212 in a first direction (i.e., counter-clockwise as shown in FIG. 4). As the second spindle 212 is rotated in the first direction, the first drive cable 232 is tensioned to affect rotation of the lower inner pulley 220 in the first direction. It will be appreciated that as the second spindle 212 is rotated to tension the first drive cable 232, the second drive cable 234 is let out to permit the rotation of the lower inner pulley 220 in the first direction. As the lower inner pulley 220 rotates in the first direction, the lower inner pulley 220 affects rotation of the upper inner pulley 224 in the first direction (i.e., clockwise as shown in FIG. 7). As the upper inner pulley 224 rotates in the first direction, the upper inner pulley 224 tensions the second idler cable 244 about the second upper idler 228 and the vertical member 64 to pivot the vertical member 64 in a counter-clockwise direction as shown in FIG. 2 about the second axis of rotation $A_2$. It will be appreciated that as the upper inner pulley 224 is rotated in the first direction to tension the second idler cable 244, the first idler cable 242 is let out to permit the vertical member 64 to pivot in the counter-clockwise direction about the second axis of rotation $A_2$.

Similarly, to pivot the vertical member 64 in a clockwise direction, as shown in FIG. 2, about the second axis of rotation $A_2$, the second drive motor 200 is energized to rotate the second spindle 212 in a second direction (i.e., clockwise as shown in FIG. 7). As the second spindle 212 is rotated in the second direction, the second drive cable 234 is tensioned to affect rotation of the lower inner pulley 220 in the second direction. It will be appreciated that as the second spindle 212 is rotated to tension the second drive cable 234, the first drive cable 232 is let out to permit rotation of the lower inner pulley 220 in the second direction. As the lower inner pulley 220 rotates in the second direction, the lower inner pulley 220 affects rotation of the upper inner pulley 224 in the second direction (i.e., counter-clockwise as shown in FIG. 7). As the upper inner pulley 224 rotates in the second direction, the upper inner pulley 224 tensions the first idler cable 242 about the first upper idler 226 and the vertical member 64 to pivot the vertical member 64 in a clockwise direction, as shown in FIG. 2, about the second axis of rotation $A_2$. It will be appreciated that as the upper inner pulley 224 rotates in the second direction to tension the first idler cable 242, the second idler cable 244 is let out to permit the vertical member 64 to pivot in the clockwise direction about the second axis of rotation $A_2$.

With continued reference to FIGS. 2-8, the third drive motor 300 manipulates the support arm 65 to pivot the horizontal member 68 about the third axis of rotation A3. The third drive motor 300 includes a third drive shaft 310 that extends through the base 61 from the upper or first side 61a to the lower or second side 61b of the base 61. The third drive shaft 310 includes a second spindle 312 that is rotatably coupled to the third drive shaft 312. The pulley assembly 90 rotatably disposed about the first axis of rotation A1 also includes a lower outer pulley 320, an outer pulley shaft 322, an upper outer pulley 324, a first upper idler 326 and a second upper idler 328.

The drive mechanism 80 includes a pair of drive cables 330 and a pair of idler cables 340 that manipulate or pivot the support arm 65 about the second axis of rotation A2. The pair of drive cables 330 includes a first drive cable 332 that has a first end 332a secured to the third spindle 312. The first drive cable 332 wraps around the second spindle 312 in the first direction (i.e., counter-clockwise as shown in FIG. 3) from end 332a. The third spindle 312 defines a first helical groove 314 that receives the first drive cable 332 as the first drive cable 332 wraps around the third spindle 312. The first drive cable 332 extends from the third spindle 312 to the lower outer pulley 320. The first drive cable 332 wraps around the lower outer pulley 320 in the first direction with a second end of the first drive cable 332 secured to the lower inner pulley 320. The lower inner pulley 320 defines a first recess 320a about the outer surface that receives the first drive cable 332. The pair of drive cables 330 also includes a second drive cable 334 that has a first end secured to the second spindle 312. The second drive cable 334 wraps around the second spindle 312 in the second direction (i.e., clockwise as shown in FIG. 3) from an end 334a. The third spindle 312 defines a second helical groove 316 that receives the second drive cable 334 as the second drive cable 334 wraps around the third spindle 312. The second drive cable 334 extends from the third spindle 312 to the lower outer pulley 320. The second drive cable 334 wraps around the lower outer pulley 320 in the second direction with a second end of the second drive cable 334 secured to the lower outer pulley 320. The lower outer pulley 320 defines a second recess 320b about the outer surface that receives the second drive cable 334.

Figure 6:
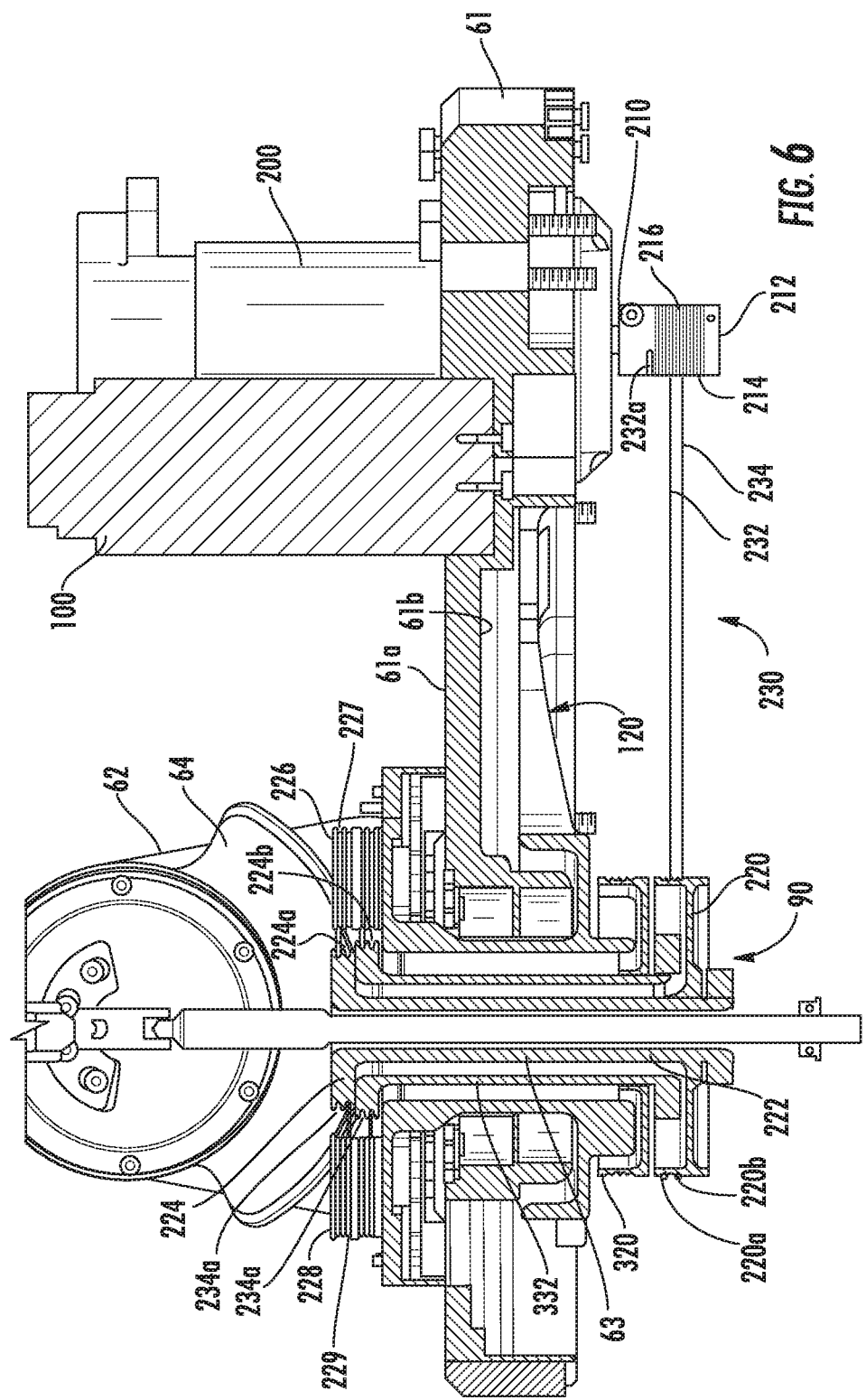
FIG. 6 is a cross-sectional view taken along section line 6-6 of FIG. 4.

The lower outer pulley 320 is rotatably fixed to the upper outer pulley 324 by the outer pulley shaft 322. The pair of idler cables 340 includes a first idler cable 342 that has a first end 342a secured to the upper outer pulley 324. The upper outer pulley 324 defines a first recess 324a that receives the first idler cable 342 that wraps around the upper inner pulley 324 in the first direction (i.e., clockwise as shown in FIG. 5). The first idler cable 342 extends from the upper outer pulley 324 to the first upper idler 326 that is rotatably supported on a post 308 of the base 61. The first upper idler 326 defines a recess 327 that receives the first idler cable 342 as the first idler cable 342 wraps around the first upper idler 326 in the first direction. The first idler cable 342 extends from the first upper idler 326 to the support arm 65. With particular reference to FIG. 6, the support arm 65 defines a first groove 65a that receives the first idler cable 342. A second end 342b of the first idler cable 342 is secured in the first groove 65a of the support arm 65. The pair of idler cables 340 includes a second idler cable 344 that has a first end 344a secured to the upper outer pulley 324. The upper outer pulley 324 defines a second recess 324b that receives the second idler cable 344 that wraps around the upper inner pulley 324 in the second direction (i.e., counter-clockwise as shown in FIG. 5). The second idler cable 344 extends from the upper outer pulley 324 to the second upper idler 328 that is rotatably supported on a post 309 of the base 61. The second upper idler 328 defines a recess 329 that receives the second idler cable 344 as the second idler cable 344 wraps around the second upper idler 328 in the second direction. The second idler cable 344 extends from the second upper idler 328 to the support arm 65. With particular reference to FIG. 5, the support arm 65 defines a second groove 65b that receives the second idler cable 344. An end 344b of the second idler cable 344 is secured in the second groove 65b of the support arm 65.

To pivot the horizontal member 68 about the third axis of rotation $A_3$, the third drive motor 300 is energized to rotate the third spindle 312 in a second direction (i.e., clockwise as shown in FIG. 4). As the third spindle 312 is rotated in the second direction, the first drive cable 332 is tensioned to affect rotation of the lower outer pulley 220 in the second direction. It will be appreciated that as the third spindle 312 is rotated to tension the first drive cable 332, the second drive cable 334 is let out to permit the rotation of the lower outer pulley 320 in the second direction. As the lower outer pulley 320 rotates in the second direction, the lower outer pulley 320 affects rotation of the upper outer pulley 324 in the second direction (i.e., counter-clockwise as shown in FIG. 7). As the upper outer pulley 324 rotates in the second direction, the upper outer pulley 324 tensions the second idler cable 344 about the second upper idler 328 and the support arm 65 to pivot the support arm 65 in a counter-clockwise direction as shown in FIG. 2 about the second axis of rotation $A_2$. It will be appreciated that as the upper outer pulley 324 is rotated in the second direction to tension the second idler cable 344, the first idler cable 342 is let out to permit the support arm 65 to pivot in the counter-clockwise direction about the second axis of rotation $A_2$. As the support arm 65 pivots in the counter-clockwise direction, the support arm 65 moves the support member 66 up which pivots the horizontal member 68 in a counter-clockwise direction as shown in FIG. 2 about the third axis of rotation $A_3$. It will be appreciated that the lower end 66a of the support member 66 is offset from the second axis of rotation $A_2$ substantially the same distance that an upper end 66b of the support member 66 is offset from the second axis of rotation $A_3$ such that as the support arm 65 rotates, the support member 66 maintains a substantially parallel relationship with the vertical member 64. It is contemplated that the support member 66 may be askew from the vertical member 64.

Similarly, to pivot the horizontal member 68 in a clockwise direction, as shown in FIG. 2, about the third axis of rotation $A_3$, the third drive motor 300 is energized to rotate the third spindle 312 in a first direction (i.e., counter-clockwise as shown in FIG. 4). As the third spindle 312 is rotated in the first direction, the second drive cable 334 is tensioned to affect rotation of the lower outer pulley 320 in the first direction. It will be appreciated that as the third spindle 312 is rotated to tension the second drive cable 334, the first drive cable 332 is let out to permit rotation of the lower outer pulley 320 in the first direction. As the lower outer pulley 320 rotates in the first direction, the lower outer pulley 320 affects rotation of the upper outer pulley 324 in the first direction (i.e., clockwise as shown in FIG. 7). As the upper outer pulley 324 rotates in the first direction, the upper outer pulley 324 tensions the first idler cable 342 about the first upper idler 326 and the support arm 65 to pivot the support arm 65 in a clockwise direction, as shown in FIG. 2, about the second axis of rotation $A_2$. It will be appreciated that as the upper outer pulley 324 rotates in the first direction to tension the first idler cable 342, the second idler cable 344 is let out to permit the support arm 65 to pivot in the clockwise direction about the second axis of rotation $A_2$. As the support arm 65 pivots in the clockwise direction, the support arm 65 moves the support member 66 down which pivots the horizontal member 68 in a clockwise direction as shown in FIG. 2 about the third axis of rotation $A_3$.

It is envisioned that the control arm 60 may also include a passive axis system for associating rotation of the swivel member 62 relative to the base 61 about the first axis of rotation $A_1$ to rotation of a gimbal supported on the end of the vertical member 68 about a gimbal axis G-G (FIG. 2) that is orthogonal to the vertical member 68. Examples of such passive axis systems are disclosed in U.S. Patent Application Ser. No. 62/345,090, and U.S. Provisional Application No. 62/345,144, entitled "PASSIVE AXIS SYSTEM FOR ROBOTIC SURGICAL SYSTEMS," the entire contents of which are incorporated herein by reference.

As detailed above and shown in FIG. 1, the user interface 40 is in operable communication with the robot system 10 to perform a surgical procedure on a patient "P"; however, it is envisioned that the user interface 40 may be in operable communication with a surgical simulator (not shown) to virtually actuate a robot system and/or tool in a simulated environment. For example, the surgical robot system 1 may have a first mode where the user interface 40 is coupled to actuate the robot system 10 and a second mode where the user interface 40 is coupled to the surgical simulator to virtually actuate a robot system. The surgical simulator may be a standalone unit or be integrated into the processing unit 30. The surgical simulator virtually responds to a clinician interfacing with the user interface 40 by providing visual, audible, force, and/or haptic feedback to a clinician through the user interface 40. For example, as a clinician interfaces with the gimbals 70, the surgical simulator moves representative tools that are virtually acting on tissue at a simulated surgical site. It is envisioned that the surgical simulator may allow a clinician to practice a surgical procedure before performing the surgical procedure on a patient. In addition, the surgical simulator may be used to train a clinician on a surgical procedure. Further, the surgical simulator may simulate "complications" during a proposed surgical procedure to permit a clinician to plan a surgical procedure.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A control arm for a robotic surgical system, the control arm comprising:
    a base;
    a swivel member rotatably supported on the base about a first axis of rotation;
    a vertical member pivotally supported on the swivel member about a second axis of rotation;
    a horizontal member pivotally supported by the vertical member about a third axis of rotation; and
    a drive mechanism disposed on the base to independently rotate the swivel member about the first axis of rotation, pivot the vertical member about the second axis of rotation, and pivot the horizontal member about the third axis of rotation, wherein the drive mechanism includes:
        a first lower pulley disposed about the first axis of rotation operably coupled to a second drive motor by a first pair drive cables; and
        a first upper pulley disposed about the first axis of rotation and rotatably fixed to the first lower pulley, the first upper pulley operably coupled to the vertical member to pivot the vertical member about the second axis of rotation.

2. The control arm according to claim 1, wherein the drive mechanism includes a first drive motor to affect rotation of the swivel member about the first axis of rotation, the second drive motor to affect pivoting of the vertical member about the second axis of rotation, and a third drive motor to affect pivoting of the horizontal member about the third axis of rotation.

3. The control arm according to claim 1, wherein the drive mechanism includes:
    a first drive motor;
    a rotation shaft disposed about the first axis of rotation and rotatably fixed to the swivel member; and
    a rotation flange including a cylindrical member disposed about the first axis of rotation and rotatably fixed to the rotation shaft, the cylindrical member operably coupled to the first drive motor to affect rotation of the swivel member about the first axis of rotation.

4. The control arm according to claim 3, wherein the rotation flange includes a web that extends to an arced wall, the arced wall forming an arc about the first axis of rotation.

5. The control arm according to claim 4, wherein the drive mechanism includes a first rotation cable and a second rotation cable that operably couple the first drive motor to the rotation flange.

6. The control arm according to claim 5, wherein the first rotation cable extends from the first drive motor in a first direction to a first end of the arced wall and the second rotation cable extends from the first drive motor in a second direction to a second end of the arced wall.

7. The control arm according to claim 1, wherein the drive mechanism includes a first idler and a second idler and the vertical member defines a first vertical member groove and a second vertical member groove, the drive mechanism further including a first pivot cable and a second pivot cable, the first pivot cable disposed about the first upper pulley, around the first idler, and within the first vertical member groove and the second pivot cable disposed about the first upper pulley, around the second idler, and within the second vertical member groove to operably couple the first upper pulley to the vertical member.

8. The control arm according to claim 1, wherein the drive mechanism includes a first pulley shaft that rotatably fixes the first lower pulley to the first upper pulley, a second lower pulley and a second upper pulley that are rotatably fixed to one another by a second pulley shaft that is disposed about the first pulley shaft.

9. A control arm for a robotic surgical system, the control arm comprising:
a base;
a swivel member rotatably supported on the base about a first axis of rotation;
a vertical member pivotally supported on the swivel member about a second axis of rotation;
a horizontal member pivotally supported by the vertical member about a third axis of rotation;
a support member and a support arm, the support arm pivotally supported by the swivel member about the second axis of rotation, the support member pivotally coupled to the support arm and the horizontal member to pivot the horizontal member about the third axis of rotation in response to pivoting of the support arm about the second axis of rotation; and
a drive mechanism disposed on the base to independently rotate the swivel member about the first axis of rotation, pivot the vertical member about the second axis of rotation, and pivot the horizontal member about the third axis of rotation, wherein the drive mechanism includes:
a drive motor;
a lower pulley disposed about the first axis of rotation operably coupled to the drive motor by a pair drive cables; and
an upper pulley disposed about the first axis of rotation and rotatably fixed to the lower pulley, the upper pulley operably coupled to the support arm to pivot the support arm about the second axis of rotation.

10. The control arm according to claim 9, wherein the drive mechanism includes a first idler and a second idler and the support arm defines a first support groove and a second support groove, the drive mechanism further including a first pivot cable and a second pivot cable, the first pivot cable disposed about the upper pulley, around the first idler, and within the first support groove and the second pivot cable disposed about the upper pulley, around the second idler, and within the second support groove to operably couple the upper pulley to the support arm.

11. A method of manipulating a control arm including a base, a swivel member rotatable relative to the base about a first axis of rotation, a vertical member pivotally supported by the swivel member about a second axis of rotation, and a horizontal member pivotally supported by the vertical member about a third axis of rotation, the method comprising:
activating a first drive motor to rotate the swivel member about the first axis of rotation;
activating a second drive motor to pivot the vertical member about the second axis of rotation, wherein activating the second drive motor to pivot the vertical member about the second axis of rotation includes rotating a first lower pulley about the first axis of rotation which affects rotation of a first upper pulley about the first axis of rotation which affects rotation of the vertical member about the second axis of rotation; and
activating a third drive motor to pivot the horizontal member about the third axis of rotation.

12. The method according to claim 11, wherein activating the first drive motor to rotate the swivel member about the first axis of rotation includes rotating a flange rotatably disposed on a lower side of the base about the first axis of rotation to rotate the swivel member.

13. The method according to claim 12, wherein rotating the flange includes wrapping a first drive cable around a drive shaft of the first drive motor and unwrapping a second drive cable from around the drive shaft of the first drive motor, wherein the first and second drive cables are disposed about an arced wall of the flange.

14. The method according to claim 11, wherein rotating the first lower pulley about the first axis of rotation includes wrapping a first drive cable about a drive shaft of the second drive motor and unwrapping a second drive cable about the drive shaft of the second drive motor.

15. The method according to claim 11, wherein activating the third drive motor to pivot the horizontal member about the third axis of rotation includes rotating a second lower pulley about the first axis of rotation which affects rotation of a second upper pulley about the first axis of rotation which affects rotation of the horizontal member about the third axis of rotation.

16. The method according to claim 15, wherein rotating the second lower pulley about the first axis of rotation includes wrapping a first drive cable about a drive shaft of the third drive motor and unwrapping a second drive cable about the drive shaft of the third drive motor.

* * * * *